US012751639B2

(12) United States Patent
Bouma et al.

(10) Patent No.: US 12,751,639 B2
(45) Date of Patent: Oct. 6, 2026

(54) METHOD AND APPARATUS FOR MEASURING INTRAVASCULAR BLOOD FLOW USING A BACKSCATTERING CONTRAST

(71) Applicant: The General Hospital Corporation, Boston, MA (US)

(72) Inventors: Brett E. Bouma, Quincy, MA (US); Nestor Uribe-Patarroyo, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/047,558

(22) PCT Filed: Apr. 18, 2019

(86) PCT No.: PCT/US2019/028068
§ 371 (c)(1),
(2) Date: Oct. 14, 2020

(87) PCT Pub. No.: WO2019/204573
PCT Pub. Date: Oct. 24, 2019

(65) Prior Publication Data

US 2021/0113101 A1 Apr. 22, 2021

Related U.S. Application Data

(60) Provisional application No. 62/659,773, filed on Apr. 19, 2018.

(51) Int. Cl.
*A61B 5/0285* (2006.01)
*A61B 5/00* (2006.01)
(Continued)

(52) U.S. Cl.
CPC .......... *A61B 5/0285* (2013.01); *A61B 5/0035* (2013.01); *A61B 5/0066* (2013.01);
(Continued)

(58) Field of Classification Search
None
See application file for complete search history.

(56) References Cited

U.S. PATENT DOCUMENTS 6,231,513 B1 5/2001 Daum
8,355,776 B2 1/2013 Milner
(Continued)

FOREIGN PATENT DOCUMENTS

JP 2017113576 A 6/2017
JP 2017524422 A 8/2017
(Continued)

OTHER PUBLICATIONS

Merkle et al. ("Dynamic contrast optical coherence tomography images transit time and quantifies microvascular plasma volume and flow in the retina and choriocapillaris", Biomedical Optics, 2016) (Year: 2016).*

(Continued)

*Primary Examiner* — Michael J Carey
*Assistant Examiner* — Marjan Saboktakin
(74) *Attorney, Agent, or Firm* — QUARLES & BRADY LLP

(57) ABSTRACT

An apparatus including: an imaging system; a probe for insertion into a vessel, the probe being coupled to the imaging system; a flow delivery system associated with the probe to release a differential-contrast fluid into the vessel at a location proximal to an end of the probe; and a processor to: collect data from the imaging system based on release of the differential-contrast fluid into the vessel, analyze the collected data to identify a presence or absence of the
(Continued)

differential-contrast fluid as a function of time, and determine a flow rate in the vessel based on analyzing the collected data.

38 Claims, 13 Drawing Sheets

(51) Int. Cl.

| | |
|---|---|
| ***A61B 5/026*** | (2006.01) |
| ***A61B 5/0275*** | (2006.01) |
| ***A61B 8/00*** | (2006.01) |
| ***A61B 8/06*** | (2006.01) |
| ***A61K 49/00*** | (2006.01) |
| ***A61K 49/22*** | (2006.01) |
| ***A61M 5/00*** | (2006.01) |

(52) U.S. Cl.
CPC .......... *A61B 5/0084* (2013.01); *A61B 5/0261* (2013.01); *A61B 5/0275* (2013.01); *A61B 8/06* (2013.01); *A61B 8/445* (2013.01); *A61B 8/481* (2013.01); *A61K 49/00* (2013.01); *A61K 49/223* (2013.01); *A61M 5/007* (2013.01)

(56) References Cited

U.S. PATENT DOCUMENTS

2004/0030220 A1 2/2004 Hamm
2008/0281205 A1* 11/2008 Naghavi ............... A61M 5/007 600/458
2009/0221920 A1* 9/2009 Boppart ............... A61B 5/6852 356/450
2010/0094133 A1* 4/2010 Yoshiara ................ A61B 8/469 600/458
2013/0317359 A1* 11/2013 Wilson ................. A61B 5/0084 600/483
2015/0051485 A1* 2/2015 Itoh .................... A61B 1/00096 600/427
2015/0283319 A1* 10/2015 Tolkowsky ........ A61B 17/3207 600/431
2017/0188831 A1 7/2017 Adler
2019/0274528 A1* 9/2019 Petroff ................. A61B 5/0084

FOREIGN PATENT DOCUMENTS

WO 2006009786 A2 1/2006
WO 2017063963 A1 4/2017

OTHER PUBLICATIONS

Textbook, fluid mechanics, 2016 (Year: 2016).*
International Searching Authority. International Search Report and Written Opinion for application PCT/US2019/28068. Mailed on Jul. 12, 2019. 7 pages.
Yaqoob, Z. et al. "Spectral domain optical coherence tomography: a better OCT imaging strategy." Biotechniques 39.6 (2005): S6-S13.
Zacharatos, H., et al. "Intravascular ultrasound: principles and cerebrovascular applications." American Journal of neuroradiology 31.4 (2010): 586-597.
Japan Patent Office, Notification of Reasons for Refusal, Application No. 2020-557221, Feb. 7, 2023, 8 pages.
Japan Patent Office, Notification of Reasons for Refusal, Application No. 2020-557221, Jun. 27, 2023, 7 pages.

* cited by examiner

1000

METHOD AND APPARATUS FOR MEASURING INTRAVASCULAR BLOOD FLOW USING A BACKSCATTERING CONTRAST

CROSS-REFERENCE TO RELATED APPLICATIONS

This application is based on, claims the benefit of, and claims priority to U.S. Provisional Application No. 62/659,773, filed Apr. 19, 2018, which is hereby incorporated herein by reference in its entirety for all purposes.

STATEMENT REGARDING FEDERALLY SPONSORED RESEARCH

This invention was made with government support under K25 EB024595 and P41 EB015903 awarded by the National Institutes of Health. The government has certain rights in the invention.

FIELD OF THE INVENTION

This invention relates generally to determinations of flow rates, and more particularly to methods and apparatus for determining intravascular flow rates based on velocity measurements obtained using backscattering contrast as measured by optical and/or ultrasonic methods.

BACKGROUND

Intravascular blood flow measurements have been challenging to obtain because of the difficulties in gaining access to the blood vessels where flow measurements are of interest. Among the most important targets are the coronary arteries, where blockages, called stenosis, can produce acute myocardial infarction, the leading cause of death in the developed world. Accurate intravascular blood flow measurements can only be acquired through the use of invasive measures because of the small size of the vessels of interest (at most a few millimeters in diameter), their location inside the body, and their complex three-dimensional structure.

Intravascular Doppler ultrasound (D-US) catheters have been developed for this purpose. However, D-US is only directly sensitive to movement in the line of sight (LOS). This represents a major drawback for accurate flow measurements, because the angle of the D-US probe inside the blood vessel is generally unknown and changes dynamically with heartbeat-induced motion. Although D-US in the Power Doppler modality is known to be sensitive to flow in all directions, there is not a known relationship between the Power Doppler reading and specific flow velocities. Usage of the Doppler Effect in optical technologies, such as optical coherence tomography, suffers from the same problems.

For reasons such as those discussed above, usage of intravascular D-US in the clinical environment has been limited. Other techniques that do not have the limitations of intravascular D-US have largely displaced its use. Among these are thermodilution techniques. Thermodilution uses the indicator-dilution framework to derive flow rates or flow velocities, where the contrast medium is a liquid at a different (generally lower) temperature that is mixed with blood at an injection site. This is the principle used in thermodilution coronary flow reserve (thermo-CFR) measurements, where the transit time of a bolus of saline at a temperature lower than circulating blood is measured using a catheter provided with a temperature transducer. Thermo- CFR cannot determine the blood flow rate, only a quantity proportional to blood flow rate. Because CFR is based on the ratio of the blood flow rate under vasodilation to blood flow rate at baseline conditions, the ratio of the transit times provides a CFR metric without the need to determine the unknown proportionality constant. However, this constant is dependent on the location of the temperature transducer and the vessel lumen area. Both quantities are expected to change, the former due to heartbeat motion, and the latter due to the lumen change under vasodilation.

Continuous thermodilution (cont-thermo) is a modification of the thermo-CFR technique in which the injectate is continuously mixed with the flowing blood at a fixed flow rate. Although cont-thermo is able to determine the blood flow rate, it can only do so under the specific conditions of the continuous saline injection. It has been shown that a continuous injection of saline, relevant for accurate measurements, produces a variable degree of vasodilation in the vessel of interest. Although this has been used to measure blood flow under vasodilation conditions, it inhibits an accurate measurement at baseline conditions and therefore cannot be used to determine an accurate CFR metric.

Finally, thermodilution techniques do not provide structural information (e.g. as is provided by imaging) about the vessels. In clinical practice imaging is highly desirable to directly assess the appearance of a given stenosis, which provides information about its vulnerability and therefore facilitates appropriate treatment. The cont-thermo catheter in particular is too large to allow an imaging catheter to be present in the vessel at the same time.

Thus, it would be desirable to have a system and a technique that overcomes one or more of the drawbacks discussed above, such as the limitations of Doppler techniques, the lack of reliable CFR measurements, and/or the limitations of continuous thermodilution, and which preferably enables intravascular imaging using the same instrumentation.

SUMMARY

Exemplary embodiments according to the present disclosure can be provided to determine flow velocities and flow rates accurately while enabling intravascular imaging, which overcome the limitations of the techniques known in the art described above.

In one exemplary embodiment, the imaging system can be configured as an optical coherence tomography ("OCT") or optical frequency-domain imaging ("OFDI") system which performs cross-sectional imaging of a first fluid such as blood in a vessel such as a blood vessel. Furthermore the imaging system can be implemented in the time-domain or in the frequency-domain by means of a spectroscopic analyzer or a wavelength-swept source. This system can perform multidimensional imaging by optical or mechanical means to acquire one-, two-, or three-dimensional imaging of the sample as a function of time. In this exemplary embodiment the first fluid can be optically coupled to the imaging system in order to collect the light scattered from the first fluid and to produce interference between reflected light and reference light, producing interferometric signals that are collected by a detector. In the present exemplary embodiment, the imaging system can be configured to deliver a second fluid (such as saline solution) having different light scattering properties into the flow of the first fluid. In the present exemplary embodiment, the imaging system can be further configured to perform an analysis of the scattered light to determine the flow velocity of the first fluid.

In another exemplary embodiment, the imaging system can be fitted to a medical catheter configured to deliver radiation that may be scattered by the first, second, or more fluids. In this exemplary embodiment, the imaging system can deliver the second fluid with different light scattering properties into the flow of the first fluid. In this exemplary embodiment, the imaging system can be a one-dimensional OCT or OFDI system that implements a scanning probe in one or more dimensions.

In another exemplary embodiment, the imaging system can be configured as an ultrasonic imaging system that performs cross-sectional imaging of a first fluid. This system can perform multidimensional imaging by electronic or mechanical means to acquire one-, two-, or three-dimensional images of the sample as a function of time. In this exemplary embodiment the first fluid can be ultrasonically coupled to the imaging system in order to collect the radiation scattered from the first fluid that is collected by a detector. In the present exemplary embodiment, the imaging system can be configured to deliver a second fluid with different ultrasonic scattering properties onto the flow of the first fluid. In the present exemplary embodiment, the imaging system can be further configured to perform an analysis of the scattered ultrasonic radiation to determine the flow velocity of the first fluid.

According to certain exemplary embodiments of the present disclosure, an exemplary method for the measured data analysis on the detected radiation will provide a flow velocity of the first, second, or more fluids.

According to certain exemplary embodiments of the present disclosure, still another exemplary method for the measured data analysis on the detected radiation will provide a flow rate of the first, second, or more fluids.

In another embodiment, an apparatus including: an imaging system; a probe for insertion into a vessel, the probe being coupled to the imaging system; a flow delivery system associated with the probe to release a differential-contrast fluid into the vessel at a location proximal to an end of the probe; and a processor to: collect data from the imaging system based on release of the differential-contrast fluid into the vessel, analyze the collected data to identify a presence or absence of the differential-contrast fluid as a function of time, and determine a flow rate in the vessel based on analyzing the collected data.

In yet another embodiment, a method including: controlling a flow delivery system associated with a probe to cause release of a differential-contrast fluid into a vessel adjacent to the probe, the probe being optically coupled to an imaging system; collecting, using a processor, data from the imaging system based on the release of the differential-contrast fluid into the vessel; analyzing, using the processor, the collected data to identify a presence or absence of the differential-contrast fluid as a function of time; and determining, using the processor, a flow rate in the vessel based on analyzing the collected data.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Before any embodiments of the invention are explained in detail, it is to be understood that the invention is not limited in its application to the details of construction and the arrangement of components set forth in the following description or illustrated in the attached drawings. The invention is capable of other embodiments and of being practiced or of being carried out in various ways. Also, it is to be understood that the phraseology and terminology used herein is for the purpose of description and should not be regarded as limiting. For example, the use herein of "including," "comprising," or "having" and variations thereof is meant to encompass the items listed thereafter and equivalents thereof as well as additional items.

Figure 1B:
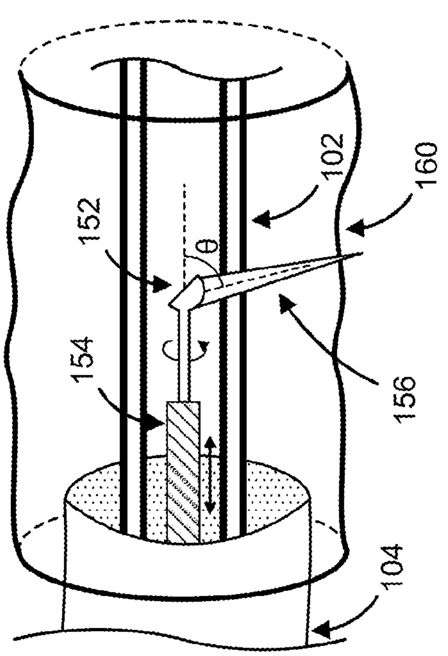
FIG. 1B shows a close up view of a distal end of a probe of the system of FIG. 1A.
Figure 1A:
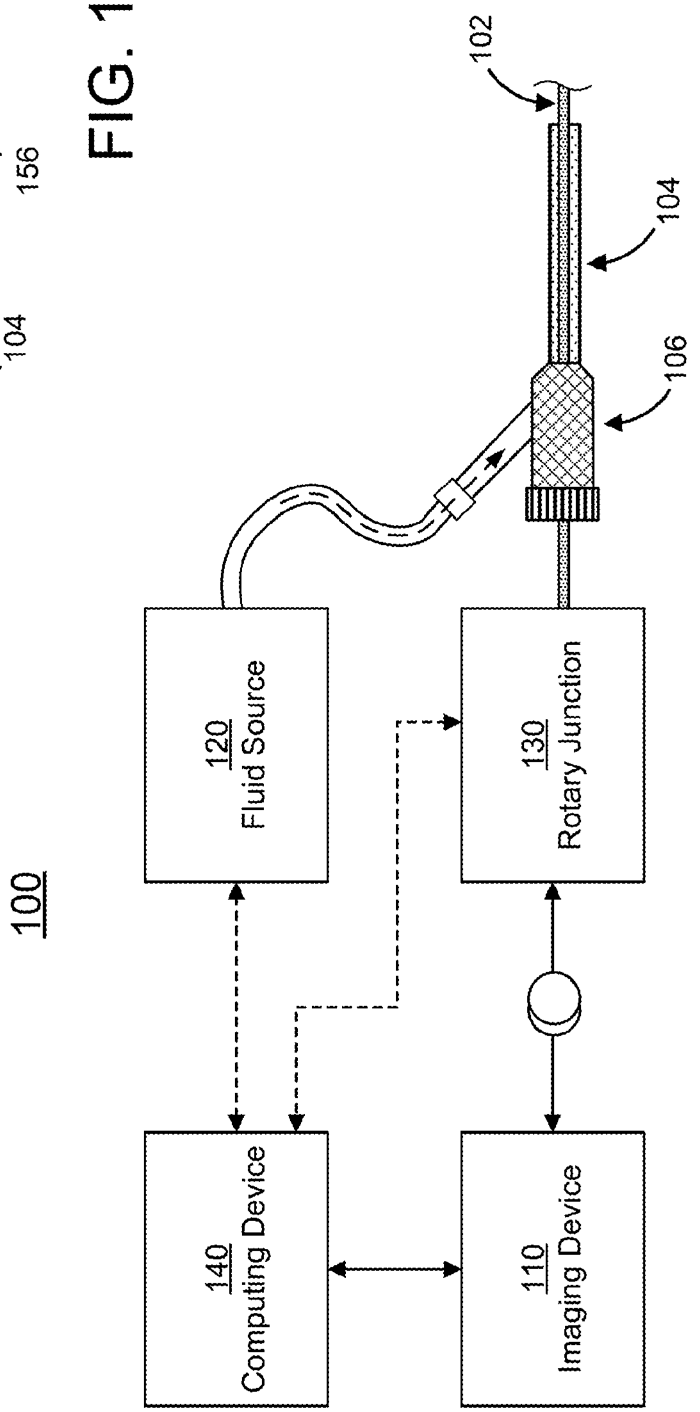
FIG. 1A shows a diagram of a fluid delivery and image collection system.
Figure 4:
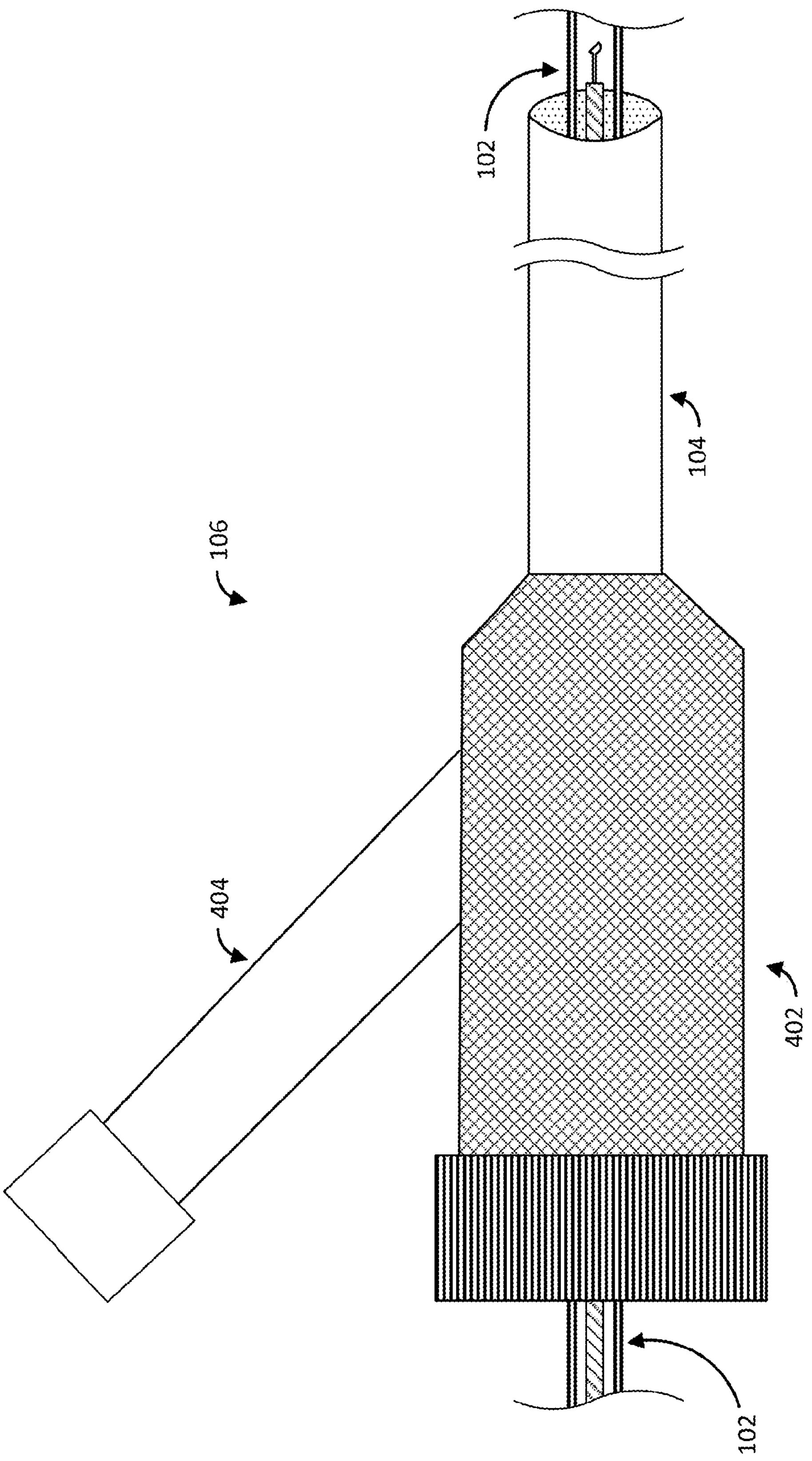
FIG. 4 shows a Y-coupler for connecting a flow delivery system to a probe.

FIG. 1A shows an embodiment of a system 100 for obtaining flow rate information. The system 100 may include a probe (e.g. optical probe 154, see FIG. 1B) which may be disposed within a sleeve 102. The sleeve 102 in turn may be inserted through a guide catheter 104 (FIG. 1A). The system 100 may include a fluid source 120 associated with the probe, for example through a Y-coupler 106 (FIG. 1A; see also FIG. 4). The fluid source 120 may be manually operated (e.g. a syringe) and/or may include a mechanical pump/power injector to deliver a fluid to a location proximal to an end of the probe. In certain embodiments, the probe may be inserted into a vessel such as a blood vessel (e.g. a coronary artery) and the fluid source 120 may be part of a flow delivery system to deliver a differential-contrast (or differential-scattering) fluid to the vessel; the rate of clearance of the fluid from the vessel can then be measured to determine a flow velocity and/or a flow rate for the vessel. In particular the flow velocity information can be combined with information regarding the cross-sectional area of the vessel to determine an absolute flow rate.

In certain embodiments, the flow delivery system includes the fluid source 120, which includes the fluid propulsion mechanism (e.g. syringe, pump, or other device for propelling fluid through the system), along with suitable tubing an connectors (including in some cases a Y-coupler 106) to deliver fluid to a vessel of interest in a controlled manner (e.g. controlled in one or more of timing, duration, and/or amount). The flow delivery system includes tubing that leads to release of the fluid at a point that is proximal to the probe end, for example from a guide catheter and/or a sleeve associated with the probe.

In various embodiments, the system 100 may also include a rotary junction 130 to rotatably couple the probe to an imaging device 110. The imaging device 110 may include an interferometric system, such as a spectral domain optical coherence tomography (SD-OCT) system or an optical frequency domain imaging (OFDI) system and the probe an OCT probe as shown in FIG. 1B and discussed further below. The imaging device 110 may be coupled to and controlled by a computing device 140 (described further below), which may in turn be coupled to and control one or both of the fluid source 120 and the rotary junction 130.

In embodiments of the invention, the probe may include elements required for collection of data such as image data. For optical imaging embodiments, the probe may include elements such as one or more optical fibers which may have one or more optical components at the end thereof, such as lens(es) or mirror(s). In the embodiment shown in FIG. 1B, the probe 154 includes optical fiber(s) which have an optical component 152 such as a ball lens at the distal end thereof. In general, the optical component 152 directs a light beam 156 at an angle θ (measured relative to the axis of the fiber(s)) towards a perimeter of the vessel 160 to collect data. The proximal end of the optical fiber(s) of the probe 154 may be optically coupled to the imaging device 110 via the rotary junction 130 (FIG. 1A) to facilitate collection of cross-sectional data from the vessel.

In certain embodiments, the probe 154 may be inserted into a vessel such as a blood vessel through which blood is flowing such that the direction of blood flow is away from the end of the probe. A fluid (e.g. a differential-contrast/differential-scattering fluid) may be released into the vessel by the fluid source at a location that is proximal to the end of the probe, i.e. closer to the operator, so that the released fluid is carried by the blood flow towards and past the probe. As the released fluid moves past the probe, the probe is controlled to collect cross-sectional image data during time periods, e.g. 30 msec or less, and the cross-sectional data may then be analyzed to determine the flow velocity and flow rate within the vessel.

Figure 2A:
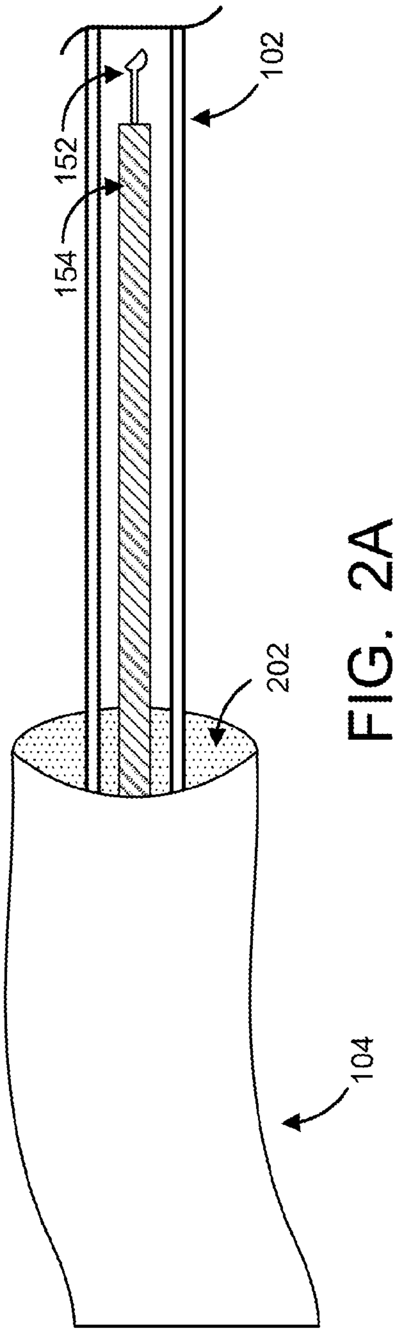
FIG. 2A shows a probe disposed within a sleeve which is disposed within a guide catheter.

In one embodiment, the probe 154 (with optical component 152 at a distal end thereof) may be disposed within a sleeve 102 which in turn may be inserted through a guide catheter 104 (FIG. 2A); the guide catheter 104 may be used to deliver differential-contrast (or differential-scattering) fluid to the vessel, e.g. through opening 202. Alternatively, or in addition, in various embodiments the sleeve 102 may include one or more openings 214 through which differential-contrast (or differential-scattering) fluid may be delivered to the vessel (FIG. 2B). There may be 1, 2, 3, 4, or any suitable number of openings 214 in the sleeve 102 and the openings 214 may be located at the same position or at staggered locations along the sleeve 102.

Figure 2C:
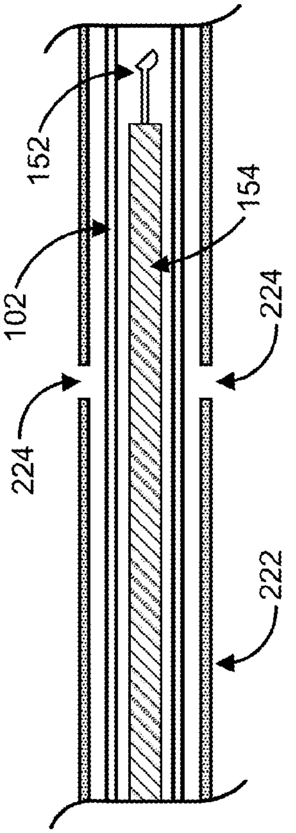
FIG. 2C shows a probe disposed within an inner sleeve which in turn is disposed within an outer sleeve, where the outer sleeve includes openings for fluid release.
Figure 2B:
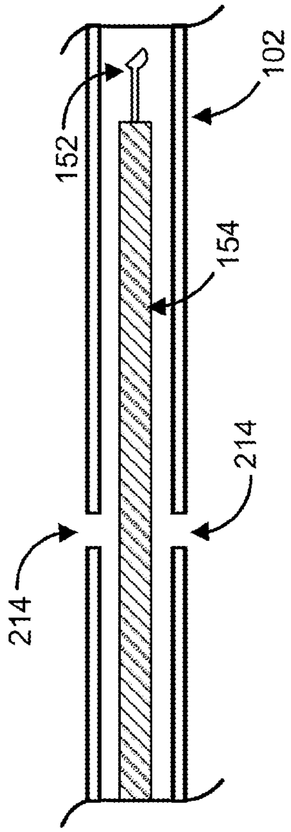
FIG. 2B shows a probe disposed within a sleeve which includes openings for fluid release.

In still further embodiments, the probe 154 may be disposed within the sleeve 102, which is an inner sleeve, and the (inner) sleeve 102 may in turn be inserted within an outer sleeve 222 (FIG. 2C). In this case, the fluid may be delivered in the space between the inner 102 and outer 222 sleeves and the openings 224 for fluid release may be located on the outer sleeve 222 to keep the fluid separate from the probe 154. In certain embodiments the double-sleeve device shown in FIG. 2C may in turn be fed through a guide catheter 104. In general, the sleeves are made from an optically transparent material to facilitate imaging through the sleeves.

Figure 3A:
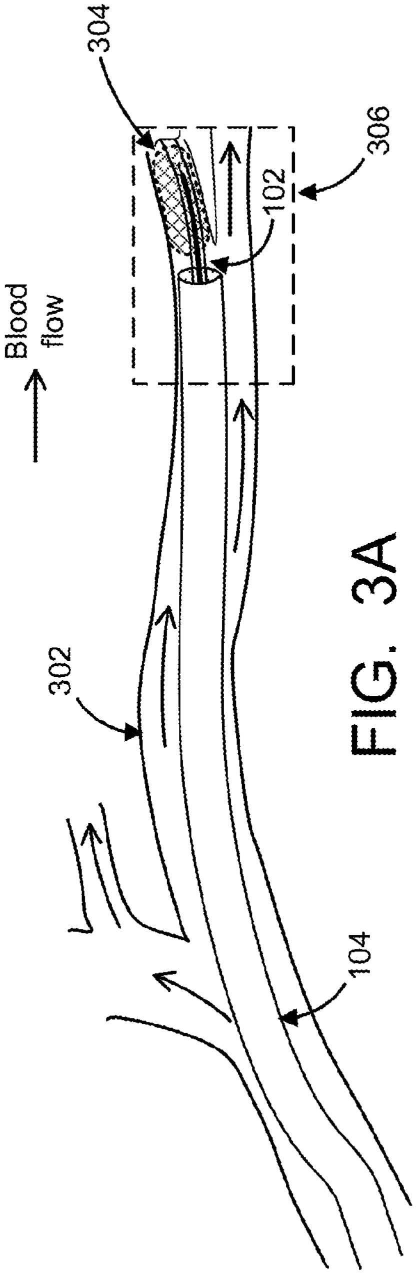
FIG. 3A shows a guide catheter having a probe and sleeve disposed therein and inserted into a vessel.
Figure 3B:
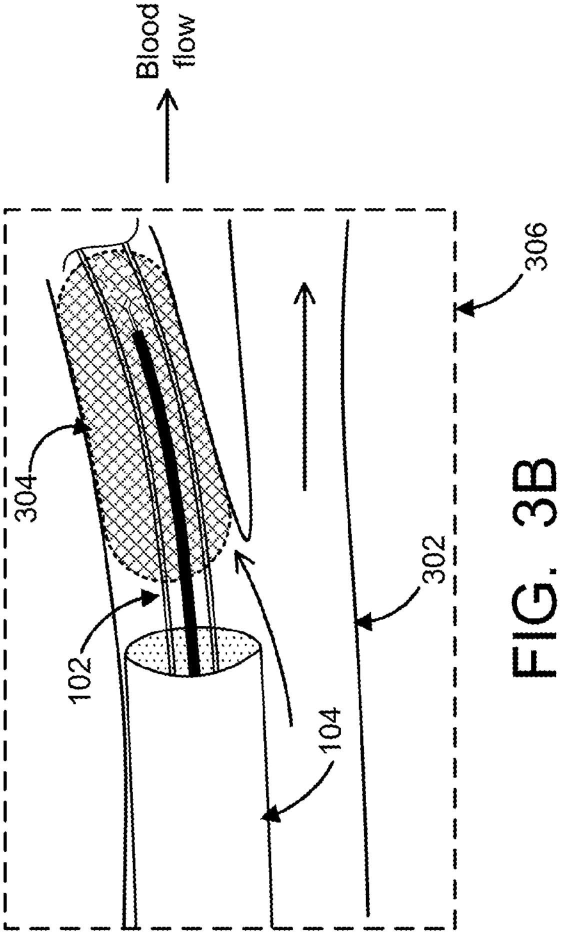
FIG. 3B shows a close up view of the end of the probe of FIG. 3A inserted into a branch of the vessel after release of a bolus of fluid into the branch through the guide catheter.
Figure 3C:
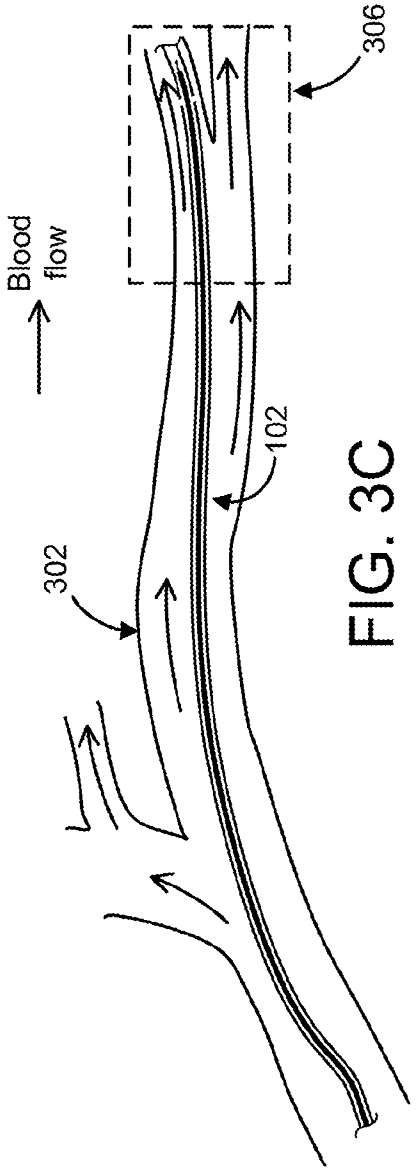
FIG. 3C shows a probe and sleeve inserted into a vessel.
Figure 3D:
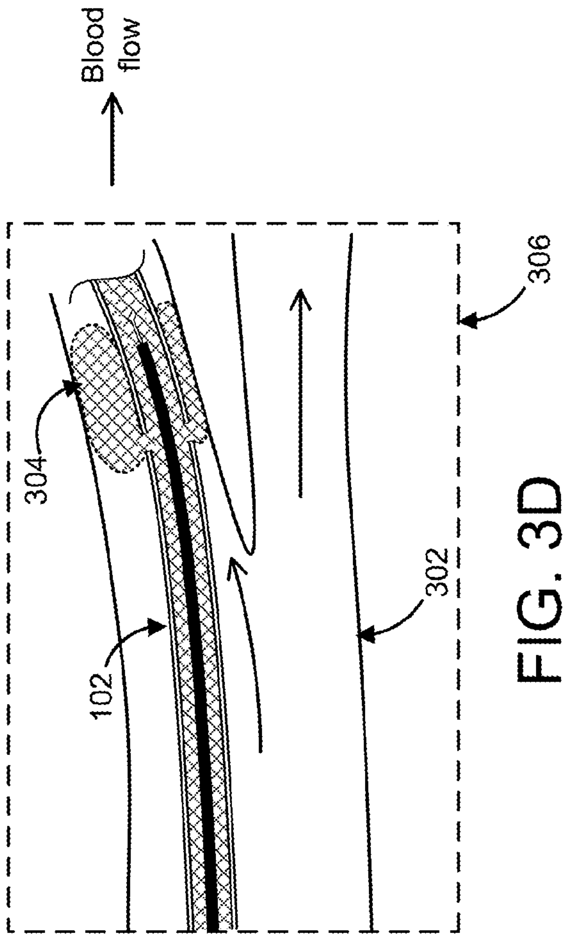
FIG. 3D shows a close up view of the end of the probe of FIG. 3C inserted into a branch of the vessel after release of a bolus of fluid into the branch through openings in the sleeve.

In use, the probe may be inserted into a vessel 302 such as a coronary artery where fluid 304 is released and measured (FIGS. 3A, 3B). In some instances a guide catheter 104 may be inserted into a larger-diameter portion of the vessel 302 and the probe (which may be inserted into a sleeve 102) may be guided into a smaller-diameter branch of the vessel, as shown in FIG. 3A and in close up in inset 306 in FIG. 3B. Once the distal end of the probe has been placed in a suitable location for gathering data, the differential-contrast (or differential-scattering) fluid 304 may be released and the movement of the fluid through the branch of the vessel 302 may be monitored by the probe to determine a flow velocity/flow rate of the branch (FIGS. 3A, 3B). As shown in FIGS. 3A and 3B, the fluid may be released from the guide catheter 104 or, as shown in FIGS. 3C and 3D, the fluid may be released from one or more openings in the sleeve associated with the probe (as shown in inset 306 in FIG. 3D). As discussed further below, data (e.g. cross-sectional images of scattering) collected by the probe before, during, and/or after release of the fluid 304 may be used to determine flow velocity/flow rate of blood in the vessel branch; the direction of blood flow in FIGS. 3A-3D is indicated by arrows within the vessels.

FIG. 4 shows an embodiment of a Y-coupler 106 such as that shown in FIG. 1A. The Y-coupler 106 may be part of a flow delivery system which is used to release differential-contrast (or differential-scattering) fluid into a vessel. The Y-coupler 106 may include a body 402 and a side branch 404 which may connect to a fluid delivery mechanism (e.g. a manual device such as a syringe or an automatic/mechanical device such as a pump) to deliver fluid to the guide catheter 104 and/or sleeve 102, while the probe and/or sleeve 102 may run straight through the Y-coupler 106. The side branch 404 may be fluidly connected to the guide catheter 104 and/or the sleeve 102 to deliver the fluid.

Figure 5A:
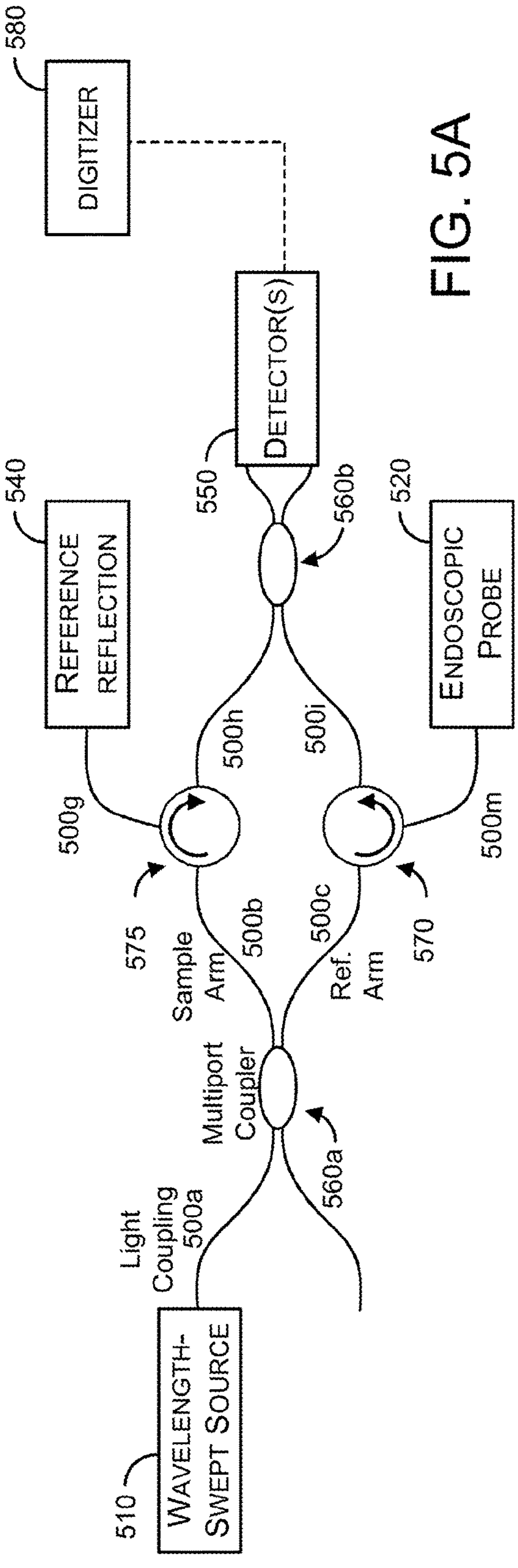
FIG. 5A shows a block diagram of an optical frequency-domain imaging (OFDI) system.
Figure 5B:
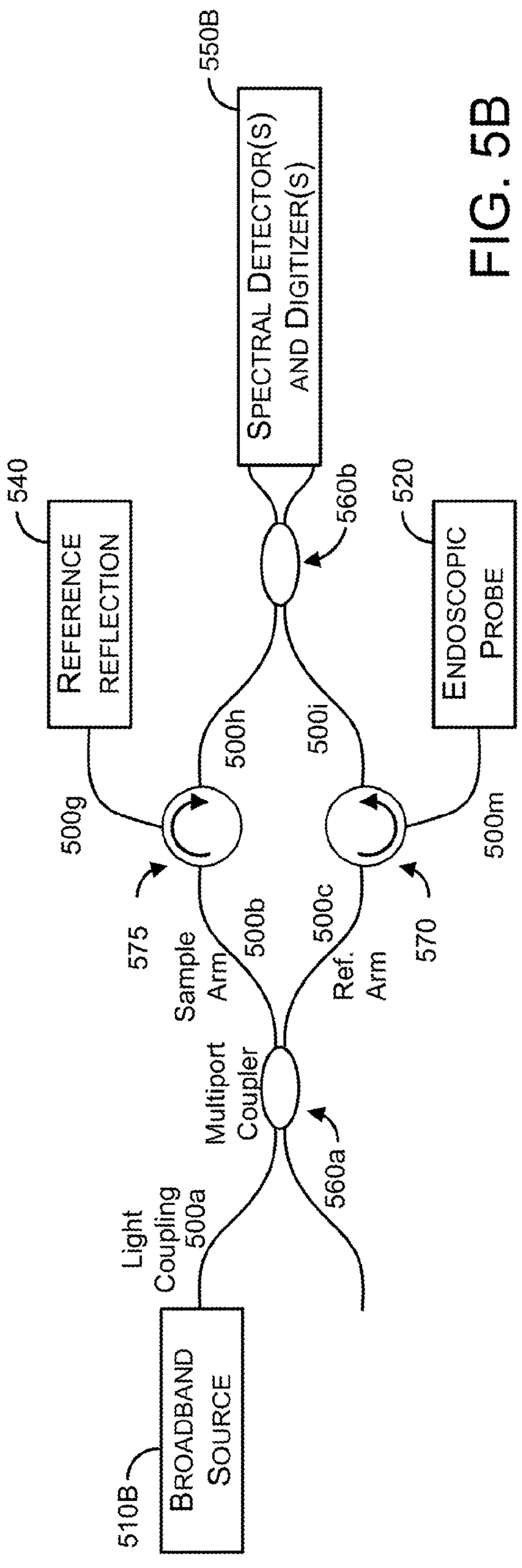
FIG. 5B shows a block diagram of an spectral-domain optical coherence tomography (SD-OCT) system.

In various embodiments, the imaging device 110 of FIG. 1A may be an interferometric imaging system such as an optical frequency domain imaging (OFDI) system (FIG. 5A) or a spectral-domain optical coherence tomography (SD-OCT) system (FIG. 5B). Although FIGS. 5A and 5B are depicted using wave-guiding components, in other embodiments these systems can be constructed using free-space optics or combinations of wave-guides and free-space optical components.

FIG. 5A shows an embodiment of an exemplary OFDI imaging system including a wavelength-swept source 510 which provides an electromagnetic signal to the multiport coupler 560*a*. This coupler can be a beam splitter, as is generally known in the art. The radiation propagates through the radiation coupling 500*a*, which can consist of free-space components or of wave-guiding components. After coupler 560*a*, radiation is separated in two couplings 500*b* and 500*c*, which make up the sample and reference arm, respectively. Radiation going into coupling 500*b* is sent into element 575, which can be a beam splitter or a circulator, as is known in the art. Coupling 500*g* provides radiation to the reference reflection 540, which is coupled back into the system via elements 500*g*, 575, and 500*h*. Similarly, radiation going into coupling 500*c* is sent into element 570, which can be a beam splitter or a circulator, as is known in the art. Coupling 500*m* provides radiation to the sample 520 through and endoscopic probe, which is coupled back into the system via 500*m*, 570, and 500*i*.

In operation of the OFDI system, sample light mixes with light from the reference reflection in the multiport coupler 560*b*, and is sent to detector assembly 550 via one or multiple couplings, depending on the use of single detectors, balanced detectors or with a system designed for polarization sensitive detection. Element 520 can be fitted with means to perform multidimensional imaging, such as lenses or scanning systems. The reference reflection 540 can have means to change the effective optical path length as is known in the art. Signal from detector assembly 550 is digitized by the digitizer 580. Due to the coherent mixing of the signals, by appropriate measurement schemes as are known in the art, it is possible to determine both the amplitude and phase of the radiation reflected from sample 520 as a function of depth, i.e. to perform cross-sectional imaging.

Other implementations of the light coupling and scanning system 520 are also possible. Specifically, in the case of OFDI systems used in cardiovascular applications, system 520 is generally configured in the form of a catheter. The sample in cardiovascular applications can be blood inside a vessel. A scanning system based on a catheter performs one-dimensional measurements of the reflectance of the sample with depth (known as A-lines) and mechanical rotation allows for scanning of the transverse plane. At the same time the catheter can be "pulled-back" to provide sectioning along the longitudinal direction to gather three-dimensional data from the sample. However, in the particular embodiments disclosed herein, the imaging probe is generally maintained in a single location, continuously imaging the same spot, to obtain information about the fluid moving through the vessel.

FIG. 5B shows an exemplary spectral-domain optical coherence tomography system consisting of a broadband source 510B which provides an electromagnetic signal to the multiport coupler 560*a*. This coupler can be a beam splitter, as is generally known in the art. The rest of the system is analogous to that in FIG. 5A, except for the detection stage, which includes a spectral detector and digitizers 550B. In various embodiments, spectral detector and digitizers 550B may include a spectrometer with associated camera and signal digitization. In various embodiments, other interferometric imaging modalities may be used in place of OFDI or SD-OCT, such as time domain OCT or circular ranging OCT.

Figure 5C:
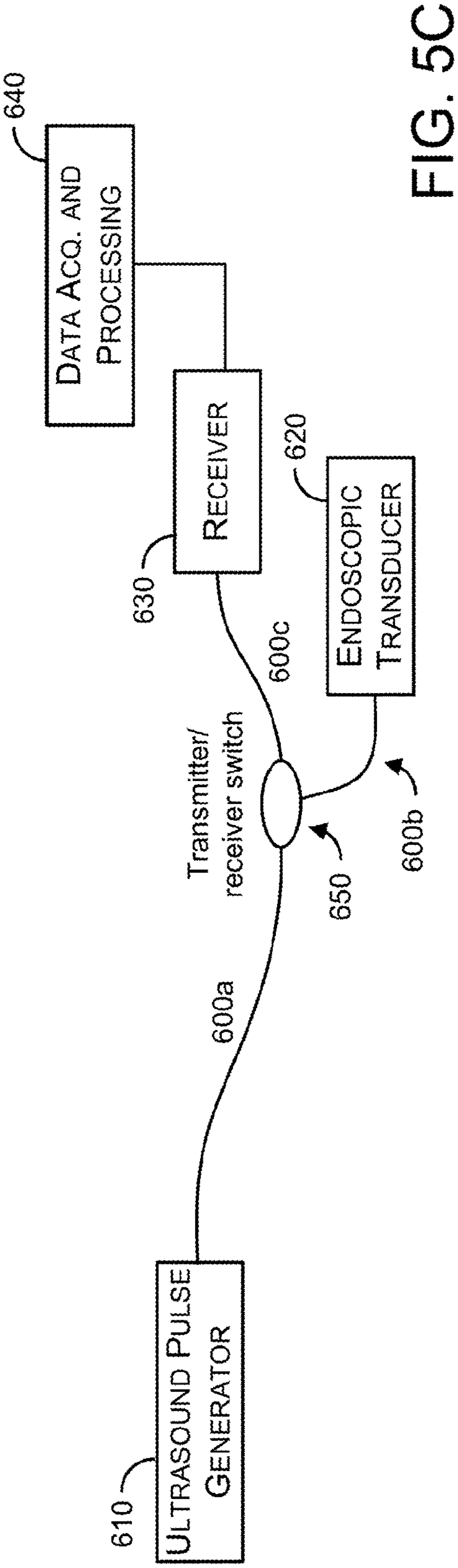
FIG. 5C is a block diagram of an endoscopic ultrasound system for use in certain embodiments.

In other embodiments, an ultrasound (e.g. intravascular ultrasound, or IVUS) probe (e.g. associated with a fluid delivery system as in FIG. 1A) may be inserted into a vessel and used to track clearance of a fluid from the vessel. FIG. 5C shows an exemplary ultrasound imaging system which includes an ultrasonic pulse generator/beamformer/amplifier system 610, which provides an electrical signal to the transmitter/receiver switch 650. The electrical signal propagates through the electrical coupling 600*a*, which can include a single cable or an array of electrical cables. Coupling 600*b* transmits/receives signal to/from the endoscopic transducer 620. Coupling 600*c* transmits the electrical signal to the receiver/amplifier/beamformer 630, which is then connected through coupling 600*d* to the data acquisition and processing unit 640. With reference to other figures herein which depict optical modalities, the endoscopic transducer 620 serves an analogous purpose to the probe 154 and optical component 152 (see as in FIG. 1B) as least with regard to directing energy which is used to generate a cross-sectional image of the vessel.

Figure 5D:
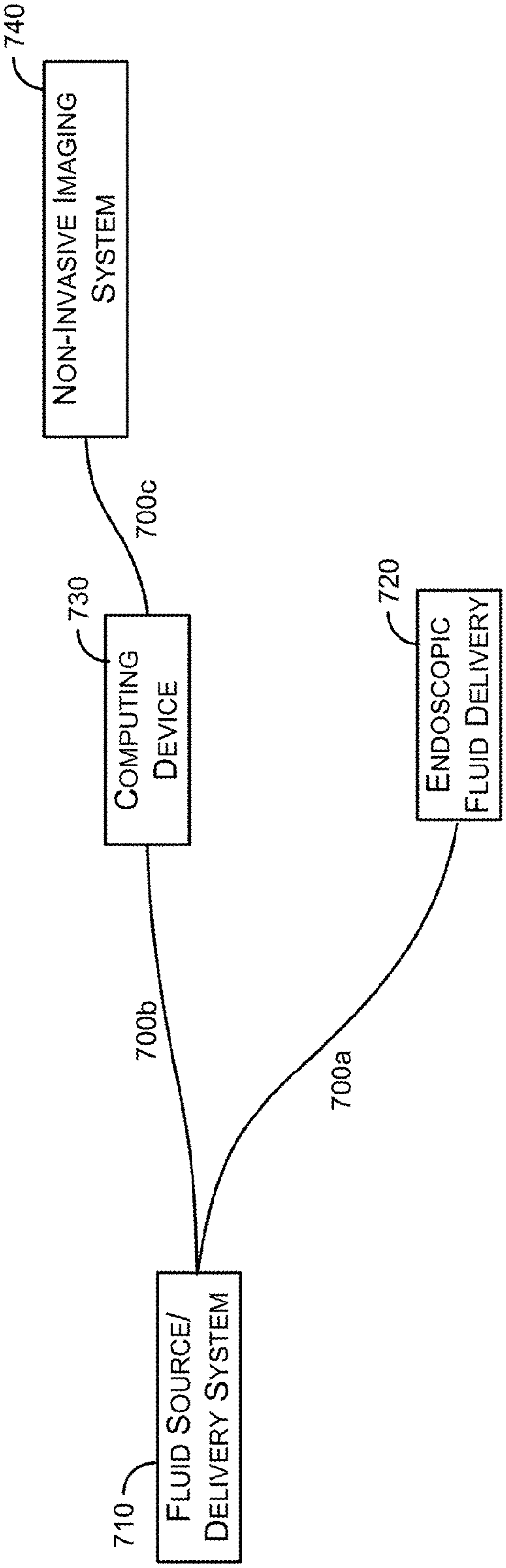
FIG. 5D is a block diagram of an embodiment using a non-invasive imaging system.

In still other embodiments, fluoroscopy, MRI, or CT may be used to monitor a vessel and track clearance of a differential-contrast (or differential-scattering) fluid as disclosed herein. For non-invasive imaging modalities such as these, a catheter or other probe mechanism may be inserted into a vessel to deliver a fluid in a particular location in a controlled manner, while imaging of the fluid delivery and clearance may be conducted non-invasively by the imaging system. FIG. 5D shown an exemplary embodiment of the present invention using a generic non-invasive imaging modality. The fluid source and delivery system 710 is coupled through connection 700*a* with the endoscopic fluid delivery system 720. Connection 700*a* is a fluid delivery connection and may, in some embodiments, also be used to deliver electrical signals to manipulate distal elements of the fluid delivery system 710 that are present in the endoscopy fluid delivery probe 720. Electrical connection 700*b* connects the fluid source and delivery system 710 with computing device 730, which is then connected through electrical connection 700*c* to the standard non-invasive imaging system 740. Computing device 730 coordinates the fluid delivery system 710 with a non-invasive imaging system 740, and can manipulate parameters related to both the fluid delivery and the image acquisition process. The non-invasive imaging system 740 may include at least one of a non-invasive ultrasound system (when measuring flow in a vessel accessible with such a system, e.g. the carotid), an Mill, a CT, and/or 2D and 3D fluoroscopy. Two-dimensional (2D) fluoroscopy can be used given some assumptions about vessel geometry, whereas three-dimensional (3D) fluoroscopy (fluoroscopy with more than one imaging plane) will necessitate fewer or no assumptions about vessel geometry.

Any of the imaging modalities disclosed herein may be used in conjunction with a flow delivery system as shown in FIG. 1A, 1B, 2A, 2B, or 2C, for example delivering fluid from a fluid source 120 under control of a manual or automatic mechanism to deliver fluid through a guide catheter 104 and/or a sleeve 102 having one or more openings therein. The flow delivery system may be associated with an imaging probe, as shown in FIG. 1A, or may be a separate component that is operated in a coordinated fashion, as shown in FIG. 5D (e.g. for use with non-invasive imaging modalities).

In general, a differential-contrast/differential scattering fluid is selected for the particular imaging modality that is used in order to provide a signal that is significantly different from blood. For interferometric imaging modalities such as OFDI or SD-OCT, blood cells provide scattering and therefore an added fluid that has a difference in scattering (higher or lower) than blood can be used to track the addition and clearance of the fluid and in turn provide a measure of flow through the vessel. The properties of the added fluid in other modalities will depend on how the modality detects blood and other fluids to provide differential contrast or scattering.

In some embodiments the fluid may have a lower signal than blood, e.g. saline, Ringer's lactate solution, dextran, or a radiopaque contrast media preferably an iodinated contrast media such as Visipaque or Omnipaque. In addition, a plurality of the kinds of the fluids may be blended. In particular embodiments, a blend of the radiopaque contrast media and saline is preferred. In other embodiments, the fluid may have a higher signal than blood, e.g. a lipid emulsion such as Intralipid (e.g. at concentrations between 1-5%), a microbubble-based solution, or one or more scattering particles (micro-spheres, micro-beads, nano-particles such as nano-rods, nano-clusters, nano-powders, etc.) which may be diluted in any of the above-listed clear media (e.g. saline, Ringer's lactate solution, dextran, or a radiopaque contrast media preferably an iodinated contrast media such as Visipaque or Omnipaque). The particular fluid that is selected is based on the imaging modality: for optical imaging including OCT and related modalities, fluids such as saline, Ringer's lactate solution, or dextran solutions may be used; for US based modalities, fluids such as microbubble-based solutions or solutions based on scattering particles may be used; for modalities such as fluoroscopy or CT, radiopaque agents such as iodinated contrast fluids including Visipaque or Omnipaque may be used; and for Mill modalities, fluids containing magnetic agents such as superparamagnetic or paramagnetic contrast agents (e.g. gadolinium) may be used.

In various embodiments, the differential-contrast (or differential-scattering) fluid is released into the vessel at a location that is "upstream" (relative to the flow direction in the vessel) of the location where measurements are made. For an imaging probe such as that shown in FIGS. 5A and 5B, fluid is released at a location that is "proximal" relative to the end of the probe, meaning in the direction of the user or operator of the probe. In contrast, the "distal" end of the probe is the end furthest from the user or operator and generally where imaging occurs. The distance between the location of fluid release and the location of imaging may vary but is generally in a range of 1 mm-10 mm, with longer distances being preferable. In various embodiments, a volume of fluid in a range of 0.1 mL to 10 mL may be released into vessel over a period of 0.1 sec to 10 sec, depending on the diameter of the vessel and the estimated flow rate of the vessel. In general, the volume may be smaller than, similar to, or larger than the volume of sample flowing per flushing time. In cases where a larger volume of fluid is delivered, the flushing time should generally be kept short so as to not substantially alter the flow rate of the sample.

In particular embodiments, the imaging modality (e.g. OCT, US, MRI, CT, or fluoroscopy) has sufficient spatial resolution so as to obtain at least about 10 samples across the inner diameter of the vessel, i.e. the modality generally has a minimum resolution of about 1/10th the inner diameter of the vessel. Thus, a cross-sectional sample through a vessel may contain an array of 10×10 voxels or pixels of data. For a vessel such as a coronary artery having an inner diameter anywhere in a range of 2.0-5.0 mm, the minimum resolution needed to obtain a 10×10 array of samples would be in a range of 0.2-0.5 mm, although using a modality with higher resolution and/or a greater number of samples is also possible. Having at least a 10×10 array of data through the cross-sectional sample helps provide sufficient data to track clearance of the added fluid with fine enough resolution to properly estimate parameters such as flushing time (see below) and vessel diameter, which in turn may be used to determine flow velocity and flow rate.

In general, data may be collected before, during, and after release of differential-contrast/differential-scattering fluid into the vessel. The data is generally from a single location in the vessel, typically a cross-sectional area, and is used to track clearing of the fluid from the vessel based on the difference in signal between the fluid and blood. Data is collected during a series of time periods to develop a time course, where the time periods may range from 1 msec to 30 msec and in general are 30 msec or less. Data from each time period (e.g. an image frame) processed to identify a fraction of the vessel's area that is occupied by fluid or blood. In some embodiments, image data may be thresholded (e.g. based on a minimum signal level associated with the presence of blood, and which consistently show this signal for a particular number of successive frames) in order to identify pixels which contain either fluid or blood.

In the case of two-dimensional cross-sectional image data, the result of the analysis may be to provide a fractional area of the vessel at each data point that has fluid. A normalized time course (e.g. data from each successive frame) of the fractional area (flushed area) can then provide an indication of the time course of flushing, which in turn indicates flow velocity in the vessel. Flow velocity can be combined with the cross-sectional area of the vessel to identify the absolute flow rate of the vessel. In some embodiments, a simpler analysis involves tracking frame mean intensity to identify the time course of flushing, although the results may be noisier than those based on the flushed area. Data based on the flushed area can be used to identify a flushing time $\tau$ which is defined as the time when the normalized flushed area reaches 0.5 and, in the Example described below, the inverse of the flushing time ($\tau^{-1}$) exhibited a linear relationship with flow rate.

An exemplary embodiment to determine the flow rate in the vessel of interest is as follows:

Identify the vessel lumen and define the area that carries the flow of interest;

Determine a threshold value that will be used to determine whether a given pixel in the image contains sample fluid or injectate. If the injectate has weaker scattering than the sample, the threshold will be implemented as a comparison of the form I>threshold, while if the injectate has stronger scattering the threshold will be implemented as a comparison of the form I>threshold;

Determine a minimum number of frames N that are required to consider a specific pixel as fully flushed;

Perform the threshold comparison on a frame-by-frame basis and assemble a collection of images showing flushed area as a function of time;

A further exemplary embodiment of the present invention might transform the image intensity into a radiation attenuation coefficient or a similar metric, as is known in the art, before performing the analyses as explained in the present invention.

Another exemplary embodiment for determining the flow velocity from the flushed area is as follows:

The average intensity of the vessel lumen as a function of time can be used to assess the signal-to-noise ratio of the measurement, by analyzing the modulation depth on the mean intensity of the image as the bolus passes;

By calculating the total area of the vessel lumen, it is possible to determine the normalized flushed area as a function of time;

The flushing time can be defined as the time it takes for 50% of the lumen area to be flushed, and can be readily calculated from the normalized flushed area as a function of time;

The inverse of the flushing time is proportional to the flow velocity. A calibration can be performed to determine the proportionality constant.

Yet another exemplary embodiment to determine the flow rate in the vessel of interest is as follows:

Calculate the area of the vessel lumen from the image;

Calculate the product of the area times the flow velocity as calculated according to the present invention;

A further exemplary embodiment for determining the flow velocity from the flushed area, when there is complete delivery of the injectate, is as follows:

Calculate the average intensity of the vessel lumen as a function of time;

Identify the frame during the bolus passage with the most homogeneous intensity in the lumen area;

The average intensity of this frame is directly related to the flow rate of the sample and the ratio of backscattering between the sample and injectate. This relation can be calibrated and used during measurements of unknown flow rates.

FIGS. 6A, 6B, 7, 8A, 8B, and 9 describe a non-limiting Example of the disclosed blood flow quantification technique based on a backscattering indicator-dilution approach, in particular using intravascular optical coherence tomography (IV-OCT). In this Example, the flow velocity is determined in a coronary artery of interest by analyzing the backscattering signal from blood after passage of a bolus of Ringer's lactate or another transparent injectate. In contrast to other techniques such as thermodilution CFR the structural OCT image can be used to determine the bolus volume and transit time, thus enabling the determination of absolute coronary flow rates with standard OCT systems. If used in conjunction with thermodilution CFR, the collected OCT images can also be used to account for motion and volume change between the two CFR flow readings, potentially improving CFR accuracy.

A small bolus (~1 mL) of transparent injectate was delivered in a short time period, fully displacing the blood as it is regularly seen during traditional OCT imaging. The time it takes for the injectate to fully disappear from the cross-sectional view (and therefore for blood to fill the vessel lumen) is proportional to the flow velocity. Once the flow velocity has been determined, the cross-sectional lumen area from the OCT image can be used to determine the absolute blood flow rate.

An intravascular (IV) OCT system (wavelength-swept laser centered at 1300 nm, 105 nm bandwidth, 54 kHz repetition rate) was used for the experiments presented in this Example. A standard guide catheter was used with an IV-OCT catheter, and imaging was performed at 3 cm from the guide catheter at 50 fps. In this Example, the guide catheter was used to flush transparent injectate into the simulated vessel. The simulated vessel (FIGS. 6A, 6B) was part of a simulated vascular system and was coupled to a fluid reservoir, a peristaltic pump, a pulse dampener, and a return reservoir. A syringe filled with injectate (e.g. saline) was coupled to the IV-OCT catheter to permit introduction of the fluid into the system upstream of the probe.

Figure 6A:
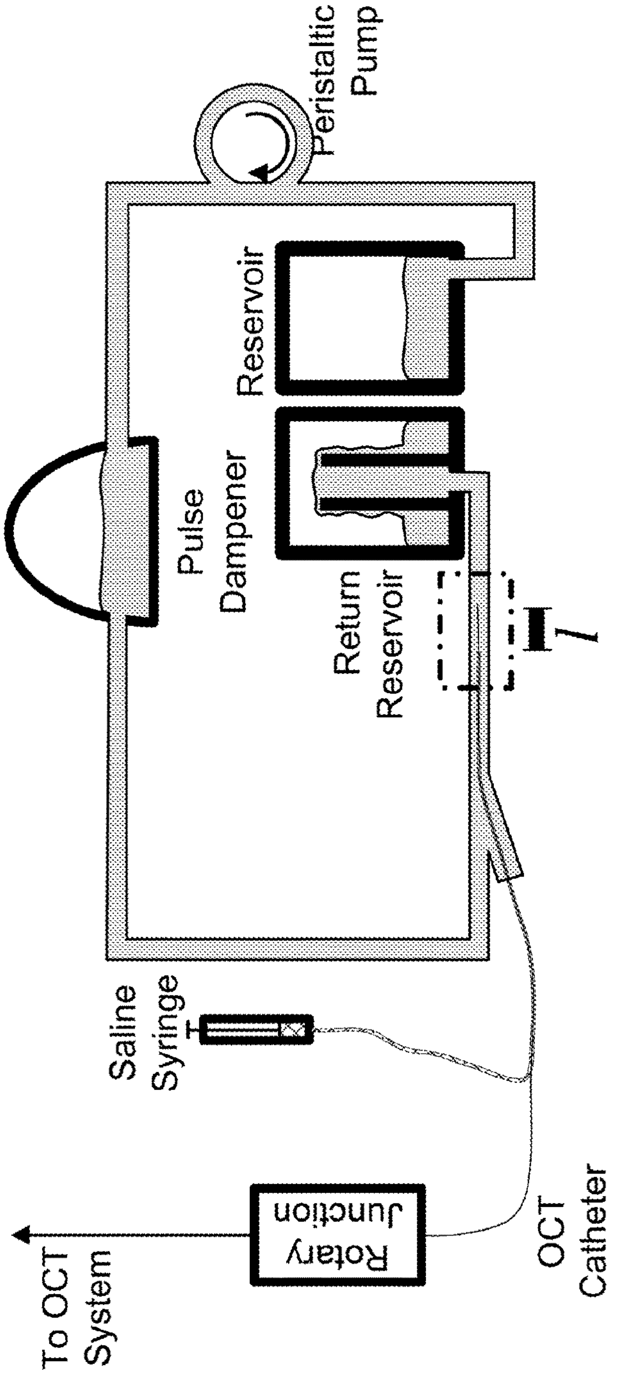
FIG. 6A shows a diagram of an experimental system for simulating and measuring blood flow.
Figure 6B:
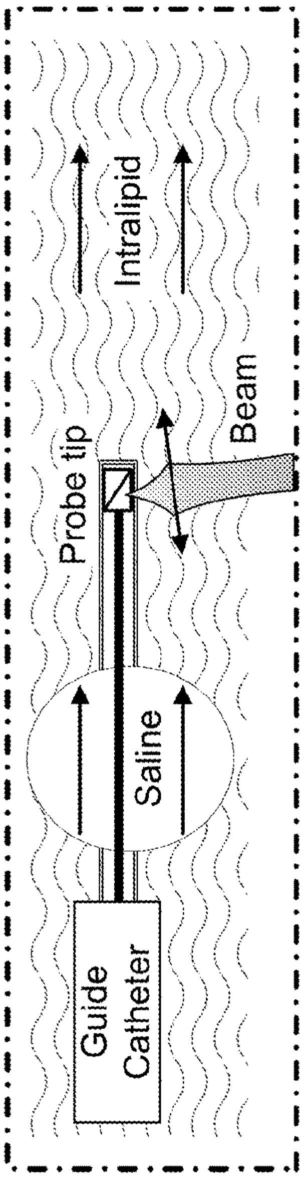
FIG. 6B shows a close up view of the region of FIG. 6A surrounding the end of the probe.

The simulated vessel contained a 2% solution of Intralipid as a blood phantom flowing in an open circuit (FIGS. 6A, 6B). Simulated flow rates of 17, 30, 43, and 57 mL/min were generated, corresponding to peak flow velocities of 70, 130, 190, and 250 mm/s in the 3.1 mm diameter section of tube into which the IV-OCT probe was inserted.

Figure 7:
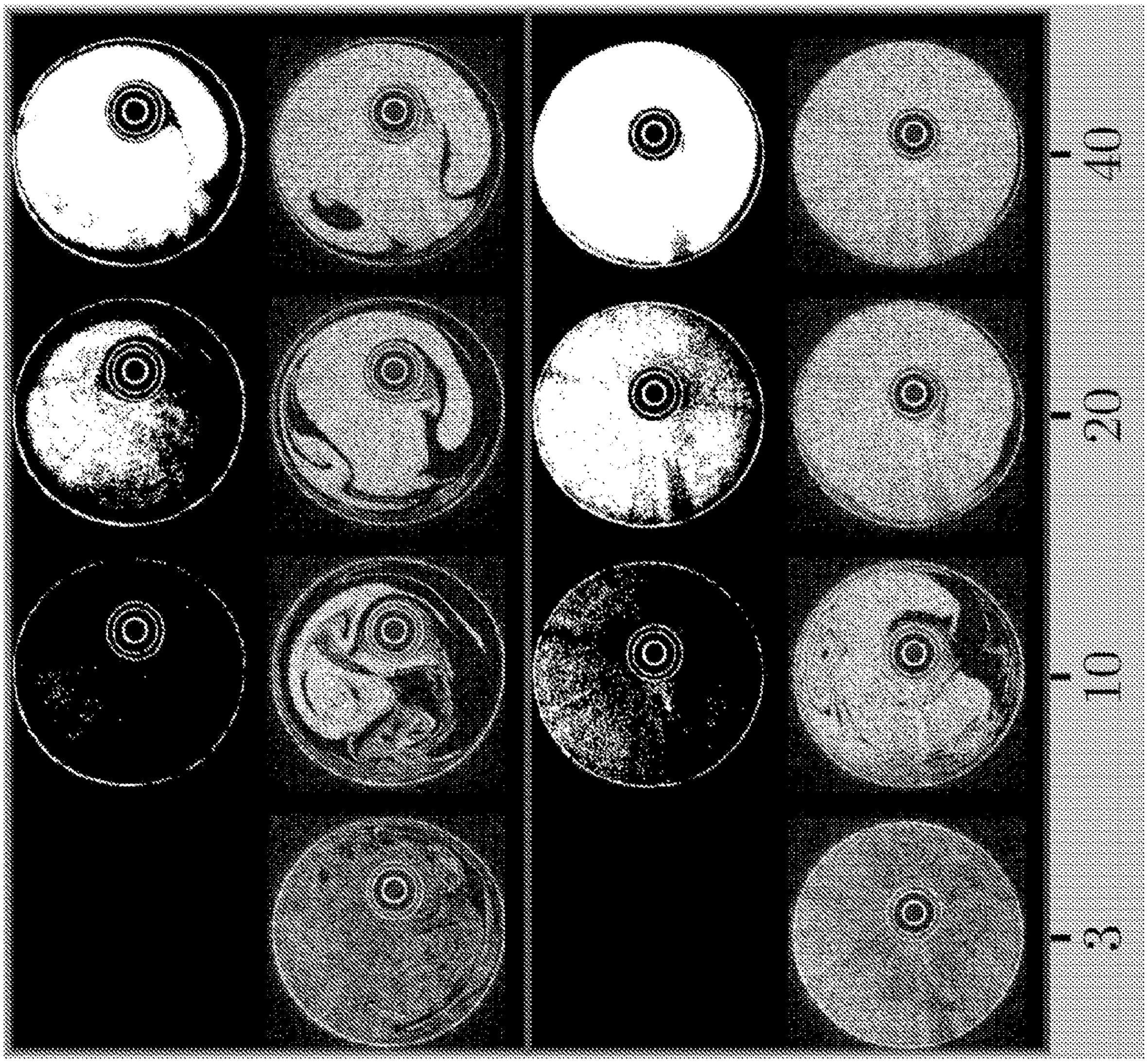
FIG. 7 shows cross-sectional image data obtained using the system of FIG. 6A.

The OCT probe was coupled to a rotary junction, permitting the probe to continuously rotate while collecting interferometric information. During experiments, the probe was rotated while fluid was released into the vessel and a series of Bscans were obtained from a fixed location in the simulated vessel. Each B scan, which uses polar coordinates, was converted into a 512×512 pixel image with Cartesian coordinates, which was then cropped to define a 200×200 pixel luminal region of interest which included the lumen of the simulated vessel (FIG. 7).

Data in the luminal region of interest was segmented for each frame, starting from the frame of minimum average intensity, i.e. the frame representing the initial bolus of injectate having the lowest scattering. For these experiments, pixels having moderate intensity (e.g. >15 dB over noise floor) for 5 or more frames were considered flushed of "blood" (i.e. Intralipid solution). Next, the fraction of flushed pixels (corresponding to the fractional area) was calculated for each frame. FIG. 7 shows a series of frames (frame nos. 3, 10, 20, and 40 as indicated at the bottom of FIG. 7) at flow rates of 17 mL/min and 57 mL/min. The bottom row in each group is the structural information for each frame and the top row shows the segmented data showing the flushed area (which recovers from the first to last frame of each group).

Figure 8A:
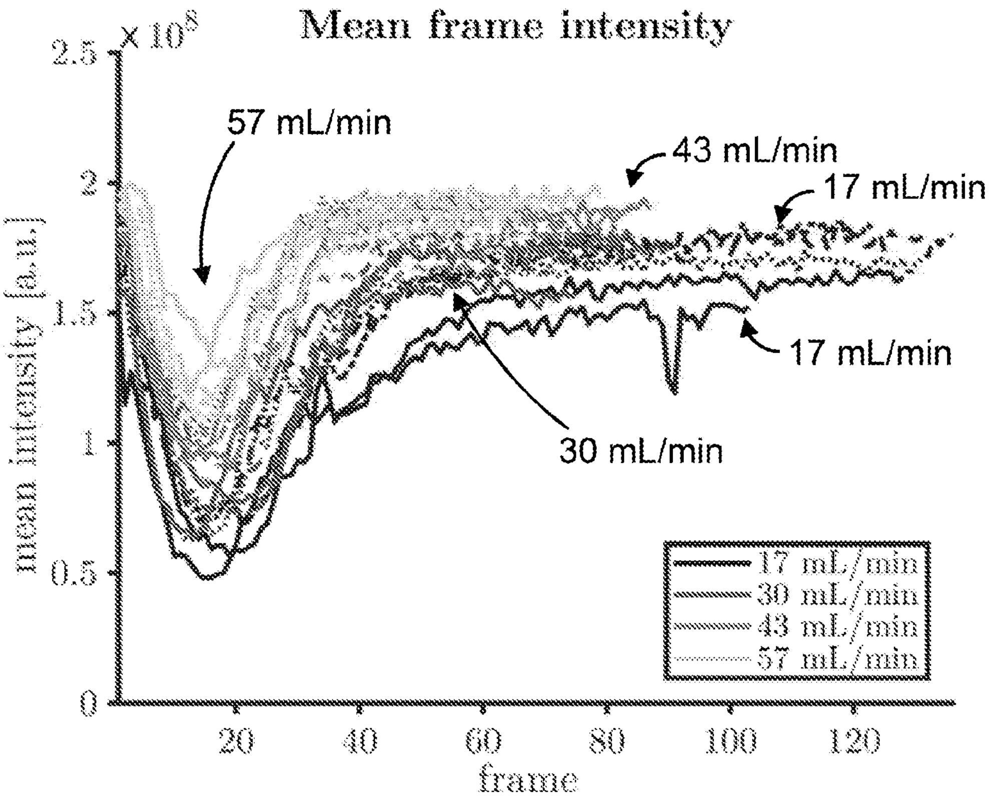
FIG. 8A shows a graph of mean frame intensity data for data such as that shown in FIG. 7 obtained using the system of FIG. 6A.
Figure 8B:
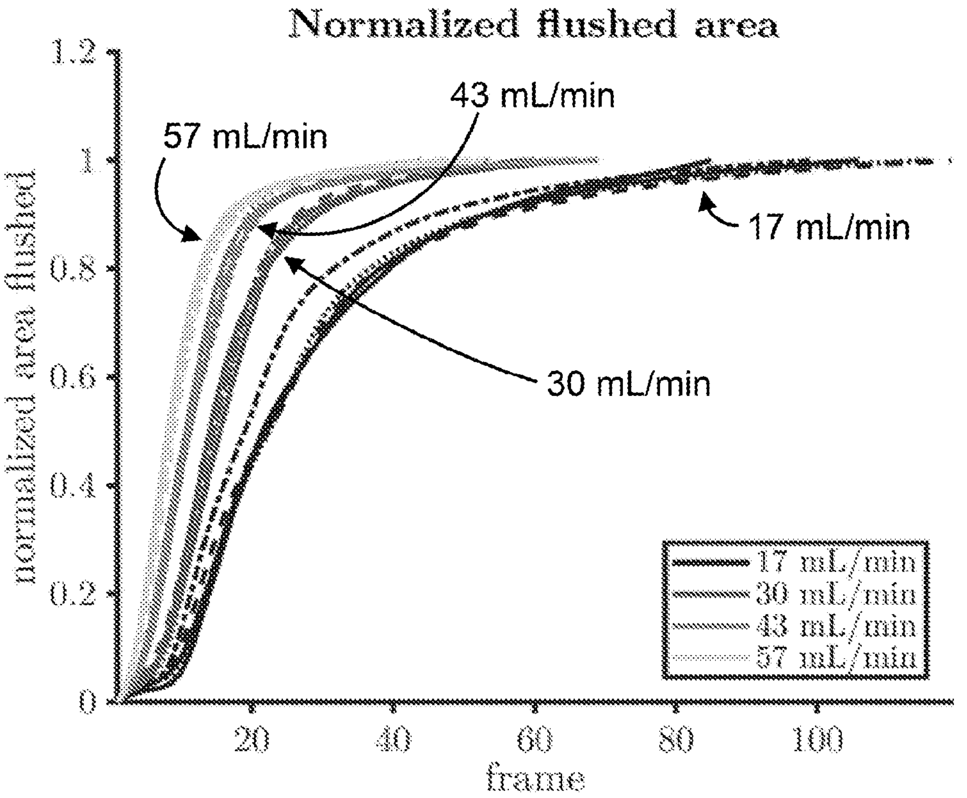
FIG. 8B shows a graph of normalized flushed area data for data such as that shown in FIG. 7 obtained using the system of FIG. 6A.
Figure 9:
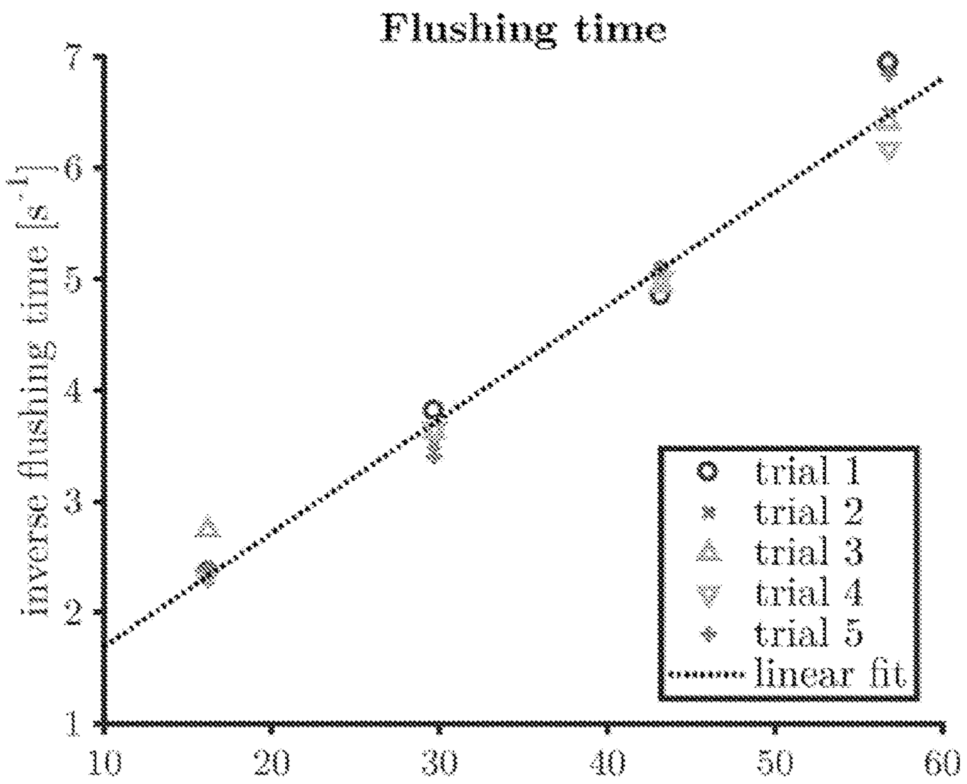
FIG. 9 shows a plot of inverse flushing time ($\tau^{-1}$) as a function of flow rate for data such as that shown in FIG. 7 obtained using the system of FIG. 6A.

FIG. 8A shows the mean frame intensity for data obtained at each of the flow rates; this data shows that mean frame intensity provides a general indication of adequate flushing but is too noisy for accurate flow determination. FIG. 8B shows that the normalized flushed area is robust and exhibits clearly differentiated behavior for different flow rates. Based on data such as that shown in FIG. 8B, the flushing time $\tau$ is defined as the time when the normalized flushed area reaches 0.5. As shown in FIG. 9, the inverse flushing time $\tau^{-1}$ exhibits a linear relationship with flow rate.

This Example shows that the disclosed techniques, which combine a straightforward flushing technique with a simplified analysis regime and which are compatible with standard OCT imaging, are capable of measuring absolute flow rates in vitro. The catheter (0.8 mm diameter) corresponds to an area stenosis of <10% in a 3 mm diameter segment, which is unlikely to decrease measured blood flow; thus the presence of the probe in the vessel does not adversely impact flow rates. Furthermore, the access to structural image information that this technique provides could make this technique more accurate than other methods such as thermo-CFR by accounting for vessel diameter and catheter location changes.

Figure 10:
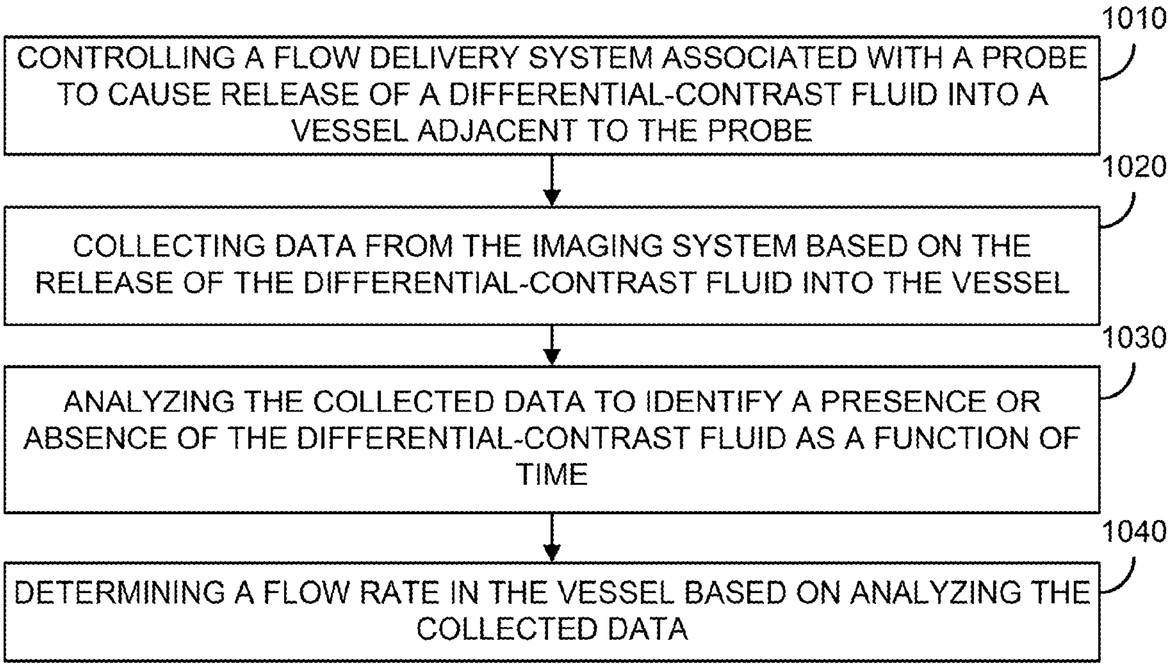
FIG. 10 shows a flow chart of a method for determining a flow rate.

FIG. 10 shows a flow chart of a method 1000 for determining a flow rate. In 1010, the method 1000 provides for controlling a flow delivery system associated with a probe to cause release of a differential-contrast fluid into a vessel adjacent to the probe, where the probe is optically coupled to an imaging system. In 1020 the method 1000 provides for collecting, using a processor, data from the imaging system based on the release of the differential-contrast fluid into the vessel. In 1030 the method 1000 provides for analyzing, using the processor, the collected data to identify a presence or absence of the differential-contrast fluid as a function of time. Finally, in 1040 the method 1000 provides for determining, using the processor, a flow rate in the vessel based on analyzing the collected data.

Figure 11:
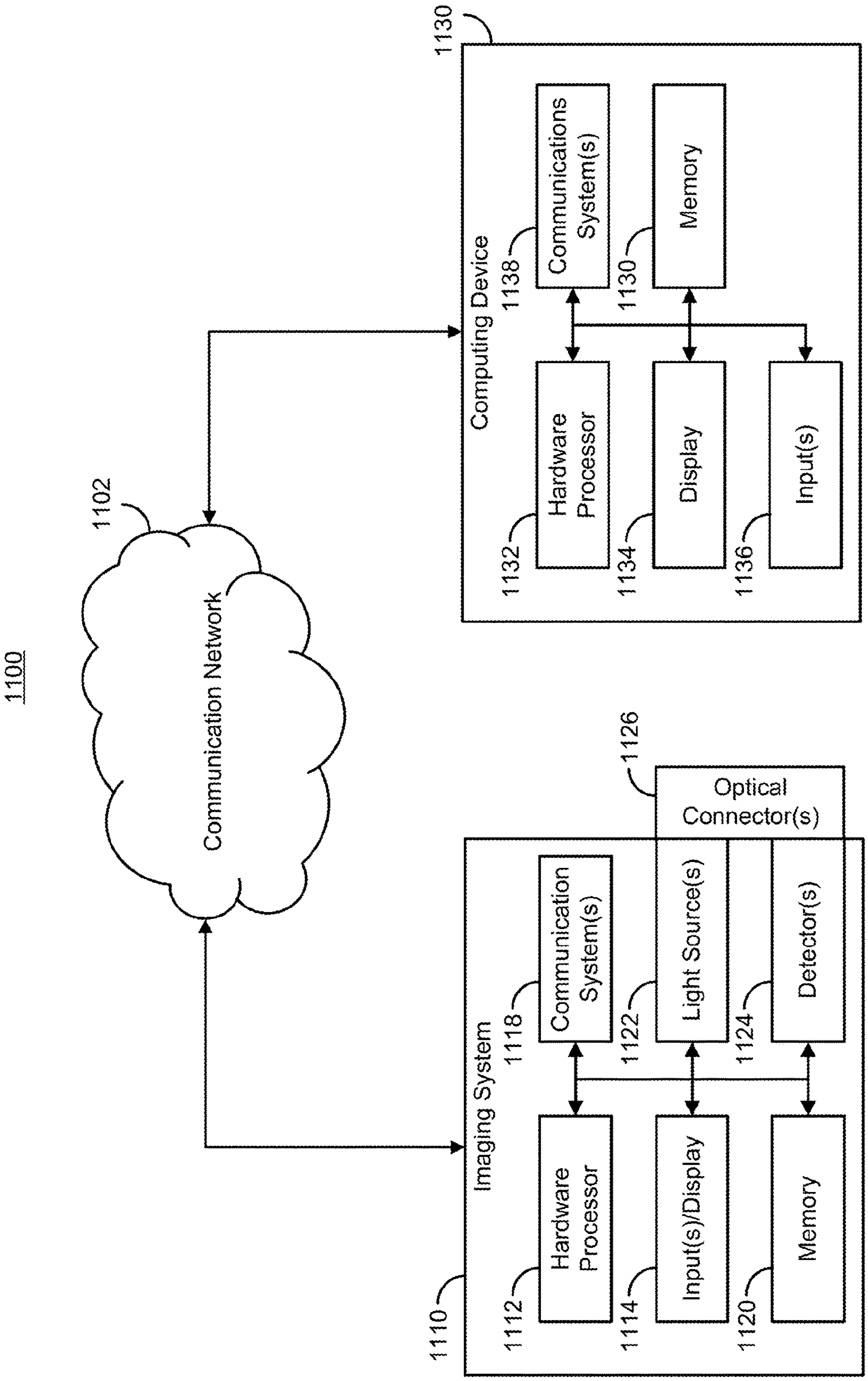
FIG. 11 shows a diagram of a computing system.

In various embodiments, the computing device 140 may be operably connected to one or more of the imaging device 110, the fluid source 120, or the rotary junction 130 to facilitate collection and analysis of data. Thus, FIG. 11 shows an example 1100 of hardware that can be used to implement an imaging device and/or a computing device that can be used in connection with some embodiments of mechanisms for determining intravascular blood flow using a backscattering contrast in accordance with some embodiments of the disclosed subject matter. For example, hardware shown in FIG. 11 can be used to implement at least a portion of spectrometer imaging device 110 and/or computing device 140. As shown in FIG. 11, in some embodiments, an imaging system 1110 can include a hardware processor 1112, a user interface and/or display 1114, one or more communication systems 1118, memory 1120, one or more light sources 1122, one or more electromagnetic detectors 1126, and/or one or more optical connectors 1126. In some embodiments, hardware processor 1112 can be any suitable hardware processor or combination of processors, such as a central processing unit (CPU), a graphics processing unit (GPU), a microcontroller (MCU), a field programmable gate array (FPGA), a dedicated image processor, etc. In some embodiments, input(s) and/or display 1114 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc.

In some embodiments, communications systems 1118 can include any suitable hardware, firmware, and/or software for communicating information over a communication network 1102 and/or any other suitable communication networks. For example, communications systems 1118 can include one or more transceivers, one or more communication chips and/or chip sets, etc. In a more particular example, communications systems 1118 can include hardware, firmware and/or software that can be used to establish a Wi-Fi connection, a Bluetooth connection, a cellular connection, an Ethernet connection, an optical connection, etc.

In some embodiments, communication network 1102 can be any suitable communication network or combination of communication networks. For example, communication network 1102 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 1102 can be a local area network, a wide area network, a public network (e.g., the Internet), a private or semi-private network (e.g., a corporate or university intranet), any other suitable type of network, or any suitable combination of networks. Communications links shown in FIG. 11 can each be any suitable communications link or combination of communications links, such as wired links, fiber optic links, Wi-Fi links, Bluetooth links, cellular links, etc.

In some embodiments, memory 1120 can include any suitable storage device or devices that can be used to store instructions, values, etc., that can be used, for example, by hardware processor 1112 to process image data generated by one or more optical detectors, to present content using input(s)/display 1114, to communicate with a computing device 1130 via communications system(s) 1118, etc. Memory 1120 can include any suitable volatile memory, non-volatile memory, storage, any other suitable type of storage medium, or any suitable combination thereof. For example, memory 1120 can include RAM, ROM, EEPROM, one or more flash drives, one or more hard disks, one or more solid state drives, one or more optical drives, etc. In some embodiments, memory 1120 can have encoded thereon a computer program for controlling operation of imaging system 1110. In some such embodiments, hardware processor 1112 can execute at least a portion of the computer program to control one or more light sources and/or detectors (e.g., to capture OCT data as described herein), to generate images and/or calculate values (e.g., an OCT image, etc.), transmit and/or receive information to/from computing device 1130, etc.

In some embodiments, imaging system 1110 can include one or more light sources 1122, such a coherent or incoherent light source (e.g., a light emitting diode or combination of light emitting diodes, a white light source, etc.), which can be a broadband light source, or a narrower band light source. For example, light source 1122 can be a wavelength-swept source as described above in connection with FIG. 5A. As another example, light source 1122 can be a broadband source as described above in connection with FIG. 5B. Additionally, in some embodiments, light sources 1122 can be associated with one or more filters.

In some embodiments, imaging system 1110 can include one or more light detectors 1124, such as one or more photodiodes, and/or one or more image sensors (e.g., a CCD image sensor or a CMOS image sensor, either of which may be a linear array or a two-dimensional array). For example, in some embodiments, detectors 1124 can include one or more detectors configured to detect light at specific wavelengths (e.g., using filters, using optics to guide light of different wavelengths to different portions of the detector(s), etc.)

In some embodiments, imaging system 1110 can include one or more optical connectors 1126. For example, such optical connectors can be fiber optic connectors configured to form an optical connection between light source(s) 1122 and/or detector 1124 and an optical fiber (e.g., as part of a fiber optic cable).

In some embodiments, computing device 1130 can include a hardware processor 1132, a display 1134, one or more inputs 1136, one or more communication systems 1138, and/or memory 1140. In some embodiments, hardware processor 1132 can be any suitable hardware processor or combination of processors, such as a CPU, a GPU, an MCU, an FPGA, a dedicated image processor, etc. In some embodiments, display 1134 can include any suitable display devices, such as a computer monitor, a touchscreen, a television, a transparent or semitransparent display, a head mounted display, etc. In some embodiments, inputs 1136 can include any suitable input devices and/or sensors that can be used to receive user input, such as a keyboard, a mouse, a touchscreen, a microphone, a gaze tracking system, motion sensors, etc.

In some embodiments, communications systems 1138 can include any suitable hardware, firmware, and/or software for communicating information over communication network 1102 and/or any other suitable communication networks. For example, communications systems 1138 can include one or more transceivers, one or more communication chips and/or chip sets, etc. In a more particular example, communications systems 1138 can include hardware, firmware and/or software that can be used to establish a Wi-Fi connection, a Bluetooth connection, a cellular connection, an Ethernet connection, etc.

In some embodiments, memory 1140 can include any suitable storage device or devices that can be used to store instructions, values, etc., that can be used, for example, by hardware processor 1132 to present content using display 1134, to communication with one or more imaging devices, etc. Memory 1140 can include any suitable volatile memory, non-volatile memory, storage, any other suitable type of storage medium, or any suitable combination thereof. For example, memory 1140 can include RAM, ROM, EEPROM, one or more flash drives, one or more hard disks, one or more solid state drives, one or more optical drives, etc. In some embodiments, memory 1140 can have encoded thereon a computer program for controlling operation of computing device 1130. In such embodiments, hardware processor 1132 can execute at least a portion of the computer program to receive content (e.g., image content) from one or more imaging devices (e.g., imaging device 1110), present content (e.g., images and/or values) transmit content to one or more other computing devices and/or imaging systems, etc.

In some embodiments, computing device 1130 can be any suitable computing device, such as a general purpose computer or special purpose computer. For example, in some embodiments, computing device 1130 can be a smartphone, a wearable computer, a tablet computer, a laptop computer, a personal computer, a server, etc. As another example, in some embodiments, computing device 1130 can be a medical device, a system controller, etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. An apparatus, comprising:
an imaging system;
an optical probe for insertion into a vessel, the optical probe being coupled to the imaging system to acquire optical data from within the vessel,
the optical probe being disposed within an inner sleeve at least partially disposed within a guide catheter;
a flow delivery system associated with the optical probe to release a differential-contrast fluid from a space between the inner sleeve and the guide catheter into the vessel at a location proximal to an end of the optical probe; and
a processor configured to:
use the optical probe to collect the optical data from the imaging system based on release of the differential-contrast fluid into the vessel,
the optical data comprising a plurality of cross-sectional images from a single vessel location to develop a time course,
analyze the collected plurality of cross-sectional images to identify a presence of the differential-contrast fluid as a function of time based on identifying pixels having an intensity above a threshold for each pixel in the plurality of cross-sectional images,
calculate a fractional area representing a fraction of pixels with intensities above the threshold for each cross-sectional image in the plurality of cross-sectional images,
normalize the plurality of cross-sectional images based on the fractional area of each cross-sectional image,
determine a flushing time based on the time course of the normalized fractional area, wherein the flushing time comprises a time from when a frame of the cross-sectional image reaches the minimum average intensity to when the normalized fractional area of the cross-sectional image reaches a particular threshold, and
determine a flow rate in the vessel based on an inverse of the flushing time.

2. The apparatus of claim 1, wherein the imaging system comprises an optical interferometric system, and
wherein the differential-contrast fluid comprises a differential-scattering fluid.

3. The apparatus of claim 2, wherein the optical interferometric system includes a reference arm, a broadband electromagnetic radiation source, and a sample arm.

4. The apparatus of claim 3, wherein the optical interferometric system comprises a spectral domain optical coherence tomography (SD-OCT) system or an optical frequency domain imaging (OFDI) system, and
wherein the optical probe is an OCT probe.

5. The apparatus of claim 4, wherein the OCT probe is a rotary probe coupled to the optical interferometric system by a rotary junction, and
wherein the processor, when collecting the optical data, is further configured to:
cause the OCT probe to rotate,
collect the data from the optical interferometric system at a plurality of radial positions, and
generate a cross-sectional image of the vessel based on collecting optical data from the optical interferometric system at the plurality of radial positions.

6. The apparatus of claim 5, wherein the processor, when collecting optical data, is further configured to:
collect the plurality of cross-sectional images through the vessel during a respective plurality of different time periods, and
wherein the processor, when analyzing the collected optical data, is further configured to:
analyze the collected optical data to identify the fractional area of each of the plurality of cross-sectional images having the differential-scattering fluid.

7. The apparatus of claim 6, wherein the processor, when analyzing the collected optical data to identify the fractional area of each of the plurality of cross-sectional images having the differential-scattering fluid, is further configured to:

determine an area of each of the plurality of cross-sectional images that has been flushed by differential-scattering fluid, and wherein the processor, when determining the flow rate, is further configured to:

determine the flow rate based on determining the area of each of the plurality of cross-sectional images that has been flushed by differential-scattering fluid.

8. The apparatus of claim 7, wherein the processor, when determining the flow rate in the vessel, is further configured to:

determine a cross-sectional area of the vessel based on the collected optical data from the optical interferometric system.

9. The apparatus of claim 6, wherein the differential-scattering fluid has a scattering property that is different from blood.

10. The apparatus of claim 9, wherein the differential-scattering fluid comprises at least one of saline, Ringer's lactate solution, dextran, lipid emulsion, or scattering particles.

11. The apparatus of claim 9, wherein the differential-scattering fluid comprises a radiopaque contrast media and saline.

12. The apparatus of claim 11, wherein the flow delivery system releases the differential-scattering fluid through an opening in a side of the inner sleeve.

13. The apparatus of claim 12, wherein the optical probe rotates within the inner sleeve.

14. The apparatus of claim 13, wherein each of the plurality of time periods is 30 msec or less.

15. The apparatus of claim 14, wherein the flow delivery system comprises a pump fluidly coupled to the guide catheter, and wherein the processor, prior to collecting the optical data, is further configured to:

control the flow delivery system to cause the release of the differential-contrast fluid into the vessel at the location proximal to the end of the optical probe.

16. The apparatus of claim 1, wherein the imaging system comprises an intravascular ultrasound (IVUS) system, and wherein the differential-contrast fluid comprises a microbubble-based media.

17. The apparatus of claim 1, wherein the flushing time is based on when the normalized cumulative cross-sectional area of the vessel flushed by the differential-contrast fluid reaches 0.5.

18. The apparatus of claim 1, wherein the threshold comprises a pixel having an intensity greater than 15 dB over a noise floor.

19. The apparatus of claim 18, wherein a pixel in a cross-sectional image is considered flushed by the differential-contrast fluid when the pixel is above the threshold in five or more cross-sectional images.

20. A method, comprising:

controlling a flow delivery system associated with a probe to cause release of a differential-contrast fluid into a vessel adjacent to the probe, the probe being optically coupled to an imaging system, and the probe being disposed within an inner sleeve at least partially disposed within a guide catheter;

collecting, using the probe in combination with a processor, optical data from the imaging system based on the release of the differential-contrast fluid from a space between the inner sleeve and the guide catheter into the vessel at a location proximal to an end of the probes, the optical data comprising a plurality of cross-sectional images from a single vessel location to develop a time course;

analyzing, using the processor, the collected plurality of cross-sectional images to identify a presence of the differential-contrast fluid as a function of time based on identifying pixels having an intensity above a threshold for each pixel in the plurality of cross-sectional images;

calculating, using the processor, a fractional area representing a fraction of pixels with intensities above the threshold for each cross-sectional image in the plurality of cross-sectional images;

normalizing, using the processor, the cross-sectional images based on the fractional area of each cross-sectional image;

determining, using the processor, a flushing time based on the time course of the normalized fractional area, wherein the flushing time comprises a time from when a frame of the cross-sectional image reaches the minimum average intensity to when the normalized fractional area of the cross-sectional image reaches a particular threshold; and determining, using the processor, a flow rate in the vessel based on an inverse of the flushing time.

21. The method of claim 20, wherein the imaging system comprises an optical interferometric system, and wherein the differential-contrast fluid comprises a differential-scattering fluid.

22. The method of claim 21, wherein the optical interferometric system includes a reference arm, a broadband electromagnetic radiation source, and a sample arm.

23. The method of claim 22, wherein the optical interferometric system comprises a spectral domain optical coherence tomography (SD-OCT) system or an optical frequency domain imaging (OFDI) system, and wherein the probe is an OCT probe.

24. The method of claim 23, wherein the OCT probe is a rotary probe coupled to the optical interferometric system by a rotary junction, and wherein collecting the optical data further comprises:

causing the OCT probe to rotate, collecting the optical data from the optical interferometric system at a plurality of radial positions, and generating a cross-sectional image of the vessel based on collecting optical data from the optical interferometric system at the plurality of radial positions.

25. The method of claim 24, wherein collecting the optical data further comprises:

collecting the plurality of cross-sectional images through the vessel at a respective plurality of different time periods, and wherein analyzing the collected optical data further comprises:

analyzing the collected optical data to identify the fractional area of each of the plurality of cross-sectional images having the differential-scattering fluid.

26. The method of claim 25, wherein analyzing the collected optical data to identify the fractional area of each of the plurality of cross-sectional images having the differential-scattering fluid further comprises:

determining an area of each of the plurality of cross-sectional images that has been flushed by differential-scattering fluid, and wherein determining the flow rate further comprises:

determining the flow rate based on determining the area of each of the plurality of cross-sectional images that has been flushed by differential-scattering fluid.

27. The method of claim 26, wherein determining the flow rate in the vessel further comprises:

determining a cross-sectional area of the vessel based on the collected optical data from the optical interferometric system, and determining the flow rate based on determining the cross-sectional area of the vessel.

28. The method of claim 25, wherein the differential-scattering fluid has a scattering property that is different from blood.

29. The method of claim 28, wherein the differential-scattering fluid comprises at least one of saline, Ringer's lactate solution, dextran, lipid emulsion, or scattering particles.

30. The method of claim 28, wherein the differential-scattering fluid comprises a radiopaque contrast media and saline.

31. The method of claim 30, wherein the flow delivery system releases the differential-scattering fluid through an opening in a side of the inner sleeve.

32. The method of claim 31, wherein the OCT probe rotates within the inner sleeve.

33. The method of claim 32, wherein each of the plurality of time periods is 30 msec or less.

34. The method of claim 33, wherein the flow delivery system comprises a pump fluidly coupled to the guide catheter, wherein the pump is controlled by the processor, and wherein, prior to collecting the optical data, the method further comprises:

controlling, by the processor, the flow delivery system to cause the release of the differential-contrast fluid into the vessel at the location proximal to the end of the probe.

35. The method of claim 20, wherein the imaging system comprises an intravascular ultrasound (IVUS) system, and wherein the differential-contrast fluid comprises a microbubble-based media.

36. The method of claim 20, wherein the flushing time is based on when the normalized cumulative cross-sectional area of the vessel flushed by the differential-contrast fluid reaches 0.5.

37. The method of claim 20, wherein the threshold comprises a pixel having an intensity greater than 15 dB over a noise floor.

38. The method of claim 37, a pixel in a cross-sectional image is considered flushed by the differential-contrast fluid when the pixel is above the threshold in five or more cross-sectional images.

* * * * *